United States Patent
Weaver et al.

[11] Patent Number: 5,911,223
[45] Date of Patent: Jun. 15, 1999

[54] INTRODUCTION OF MODIFYING AGENTS INTO SKIN BY ELECTROPORATION

[75] Inventors: James C. Weaver, Sudbury, Mass.; Tani Chen, Piqua, Ohio; Christopher Cullander, Berkeley, Calif.; Richard Guy, Annecy-le-Vieux, France; Robert S. Langer, Newton, Mass.; Thomas E. Zewert, Boston, Mass.; Uwe Pliquett, Bielefeld-Grossdornberg, Germany; Rita Vanbever, Brussels, Belgium; Mark R. Prausnitz, Atlanta, Ga.

[73] Assignees: Massachusetts Institute of Technology, Cambridge, Mass.; The Regents of the University of California, Oakland, Calif.

[21] Appl. No.: 08/695,367

[22] Filed: Aug. 9, 1996

[51] Int. Cl.[6] .................................................. A61B 19/00
[52] U.S. Cl. ............................... 128/898; 604/20; 607/3; 607/901
[58] Field of Search .................................... 604/20, 890.1, 604/21, 50, 49, 19; 607/3, 901; 128/898

[56] References Cited

U.S. PATENT DOCUMENTS

| | | |
|---|---|---|
| 578,611 | 3/1897 | Rively . |
| 3,078,850 | 2/1963 | Schein et al. . |
| 3,614,955 | 10/1971 | Mirowski et al. . |
| 3,680,544 | 8/1972 | Shinnick et al. . |
| 4,055,799 | 10/1977 | Coster et al. . |
| 4,081,340 | 3/1978 | Zimmermann et al. . |
| 4,154,668 | 5/1979 | Zimmermann et al. . |
| 4,220,916 | 9/1980 | Zimmermann et al. . |

(List continued on next page.)

FOREIGN PATENT DOCUMENTS

| | | | |
|---|---|---|---|
| 01011564 | 1/1989 | Japan ............................... | A61N 1/30 |
| 64-11564 | 1/1989 | Japan ............................... | A61N 1/30 |

OTHER PUBLICATIONS

Mir et al., "Pharmacological Applications of Electropermeaization of Living Cells", *Lab. De Biochimie–Enzymologie, Institute Gustave–Roussy 94805 Villejuif Cadex—France.*

Zewert et al., "Transdermal Transport of DNA Antisense Oligonucleotides by Electroporation", *Biochemical and Biophysical Research Communications* 212:286–292 (1995).

Scott et al., "Transport of Ionic Species in Skin: Contribution of Pores to the Overall Skin conductance", *Pharmaceutical Research* 10:1699–1709 (1993).

(List continued on next page.)

*Primary Examiner*—David H. Willse
*Assistant Examiner*—Kelly O'Hara
*Attorney, Agent, or Firm*—Hamilton, Brook, Smith & Reynolds, P.C.

[57] ABSTRACT

A method of modifying epidermis for transport of a material by electroporation includes applying to epidermis an agent that, upon entry into the epidermis, will modify the epidermis to thereby cause and altered rate of transport of a material across the epidermis. Typically, the altered rate will be an increased rate of transport. The epidermis is electroporated, whereby at least a portion of the modifying agent enters the electroporated epidermis, thereby modifying the epidermis to cause an altered rate of transport of a material across the epidermis. In another embodiment, the modifying agent can modify the epidermis to enable measurement and/or monitoring of physiological conditions or change within or beneath the epidermis. The modifying agents can also be employed to facilitate discharge of fluids from within an organism, such as by providing pathways for discharge of fluids from a tumor. Examples of modifying agents include: oxidizing agents; reducing agents; particles, such as optical indicator beads or beads that include drugs to be released into tissue; electrically-charged particles or molecules; etc. Materials that can be transported by the method of the invention include, for example, proteins, nucleic acids, electrically charged molecules or particles, microorganisms suitable for immunization, etc. Also, tissues other than skin can be employed in the method of the invention.

49 Claims, 1 Drawing Sheet

U.S. PATENT DOCUMENTS

| | | |
|---|---|---|
| 4,411,648 | 10/1983 | Davis et al. . |
| 4,578,168 | 3/1986 | Hofmann . |
| 4,663,292 | 5/1987 | Wong et al. . |
| 4,695,547 | 9/1987 | Hilliard et al. . |
| 4,764,473 | 8/1988 | Matschke et al. . |
| 4,784,737 | 11/1988 | Ray et al. . |
| 4,822,470 | 4/1989 | Chang . |
| 4,955,378 | 9/1990 | Grasso . |
| 4,979,948 | 12/1990 | Geddes et al. . |
| 5,007,995 | 4/1991 | Takahashi et al. . |
| 5,019,034 | 5/1991 | Weaver et al. . |
| 5,047,007 | 9/1991 | McNichols et al. . |
| 5,098,843 | 3/1992 | Calvin . |
| 5,115,805 | 5/1992 | Bommannan et al. ............... 604/20 X |
| 5,137,817 | 8/1992 | Busta et al. . |
| 5,279,543 | 1/1994 | Glikfeld et al. . |
| 5,296,222 | 3/1994 | Petersen et al. . |
| 5,298,017 | 3/1994 | Theeuwes et al. . |
| 5,323,769 | 6/1994 | Bommannan et al. ............... 604/20 X |
| 5,362,307 | 11/1994 | Guy et al. ................................. 604/20 |
| 5,383,848 | 1/1995 | Hillman et al. . |
| 5,389,069 | 2/1995 | Weaver . |
| 5,445,609 | 8/1995 | Latin et al. . |
| 5,462,520 | 10/1995 | Hofmann et al. . |
| 5,547,467 | 8/1996 | Pliquett et al. . |
| 5,667,491 | 9/1997 | Pliquett et al. ............................ 604/50 |

OTHER PUBLICATIONS

Mir et al., "Electrochemotheraph Potentiation of Antitumour Effect of Bleomycin by Local Electric Pulses", *Eur. F. Cancer* 27(1):68–72 (1991).

Okino et al., "Effects of a High–Voltage Electrical Impulse and an Anticancer Drug on In Vivo Growing Tumors", *Jpn. J. Cancer Res.* 78(12):1319–1321 (1987).

Heroux et al., "Assessment of Trauma in tissues By Electrica Impedance Measurements", *Electromagnetics in Biology and Medicine*, pp. 215–221 (1991).

Bhatt et al., "Rhabdomyolysis due to Pulsed Electric Fields" *Plastic and Reconstructive Surgery* 86(1):1–11 (1990).

Heller et al., "Transfer of Human Membrane Surface Components by Incorporating Human Cells into Intact Animal Tissue by Cell Tissue Electrofusion In Vivo", *Biochimica et Biophysica Acta* 1024:185–188 (1990).

Titomirov et al., "In Vivo Electroporation and Stable Transformation of Skin Cells of Newborn Mice by Plasmid DNA", *Biochimica et Biophysica Acta.* 1088:131–134 (1991).

Okino, et al., *Journal of Japan Soc. For Cancer Therapy* 22(8):337 (1987).

Kanesda, et al., *Journal of Japan Soc. For Cancer Therapy* 22(8):338 (1987).

Okino et al., *Japan Journal of Cancer Research* 46:420 (1987).

Weaver, "Electroporation: A General Phenomenon for Manipulating Cells and Tissues", *Journal of Cellular Biochemistry* 51:426–435 (1993).

Prausnitz et al., "Electroporation of mammalian skin: A mechanism to enhance transdermal drug delivery", *Proc. Natl. Acad. Sci. USA* 90:10504–10508 (1993).

Prausnitz et al., "Methods for in Vivo Tissue Electroporation Using Surface Electrodes", *Academic Press, Inc. Drug Delivery* 1:125–131 (1993).

Bergan et al., "Electroporation enhances c–myc antisense oligodeoxynucleotide efficacy", *Nucleic Acids Research* 21(15):3567–3573.

Zewert et al., "Transdermal Transport of DNA Antisense Oligonucleotides by Electroporation", *Biochemical and Biophysical Research Comm.* 212(2):286–292.

Zimmermann et al., "Effects of External Electrical Fields on Cell Membranes", *Bioelectrochemistry and Bioenergetics* 3:58–83 (1976).

Tamada et al., "Measurement of Glucose in Diabetic Subjects Using Noninvasive Transdermal Extraction", *Nature Medicine* 1:1198–1202 (1995).

Dinh et al., "Upper and Lower Limits of Human Skin Electrical Resistance in Iontophoresis", *American Institute of Chemical Engineers Joural* 39(12):2011–2018 (1993).

Pliquett et al., "Imaging of Fluorescent Molecules and Small Ion Transport Through Human Stratum Corneum During High–Voltage Pulsing: Localized Transport Regions are Involved", *J. Biophysical Chemistry* 58:185–204 (1996).

Pliquett et al., "Changes in the Passive Electrical Properties of Human Stratum Corneum Due to Electroporation", *Biochemica et Biophysica Acta* 1239:111–121 (1995).

Edwards et al., "Analysis of Enhanced Transdermal Transport by Skin Electroporation", *Journal of Controlled Release* 34:211–221 (1995).

INTRODUCTION OF MODIFYING AGENTS INTO SKIN BY ELECTROPORATION

RELATED APPLICATION

This is an application claiming priority to Provisional Application Ser. No. 60/002,219, filed on Aug. 11, 1995, the entire teachings of which are incorporated herein by reference.

GOVERNMENT FUNDING

This invention was made with Government support under Grant No. DAAL03-090-G-0218 awarded by the Department of the Army, and under Grant Nos. NIH-5R01-GM34077 and HD 27839, awarded by the National Institutes of Health. The Government has certain rights in the invention.

BACKGROUND OF THE INVENTION

Delivery and retrieval of molecules and/or ions of fluids into or through skin tissue is an accepted method for many types of therapeutic and diagnostic treatment, and has led to an increased interest in transdermal drug delivery. Generally, transfer of fluids, particularly those containing macromolecules, through skin tissue is achieved by use of a hypodermic needle. However, use of hypodermic needles can be painful, and provides relatively little control for drug delivery. Also, in the case of treating diseased tissue, the effect of chemical agents on the diseased tissue is often dependent upon delivery of the chemical agent across cell membranes of the cells in the tissue mass, as opposed to simply injecting the chemical agent into the tissue. Further, chemical agents which are injected into diseased tissue typically enter the bloodstream and are transported away from the targeted tissue mass before they have a significant therapeutic effect on the tissue mass into which they were injected. Also, there are many problems that are often associated with treatment of cells by conventional methods, such as by intravenous injection. For example, the cells of melanoma tumors are typically difficult to target by injection techniques because they are in the form of relatively thin tissue. Further, injections can traumatize tissue, thereby possibly spreading potentially malignant growth. In addition, use of some types of intravenous injection, such as those which employ intravenous infusion pumps, can be difficult to control and can promote infection. This complication is especially significant for patients afflicted with immunocompromising illnesses (e.g., leukemias and HIV infection).

One attempt to solve problems presented by transfer of molecules and/or ions across tissues, in particular skin tissue, is employment of a phenomenon called electroporation. Generally, electroporation is a method of temporarily or permanently increasing the permeability of tissue and cell membranes, and of simultaneously providing an electrical driving force. The increased permeability allows transport or migration, of chemical agents through the tissue or across cell membranes into cells. Electroporation has been used to deliver drugs to tissue, in vivo, by applying electrodes to the surface of an organism and applying a voltage between the electrodes which exposes the tissue to an electric field. The tissue becomes electroporated and allows delivery of a chemical agent, such as a drug, which has been applied either topically to the organism or injected into the bloodstream of the organism, across the electroporated tissue and into cells of the electroporated tissue.

The effect of electroporation on tissue can be temporary or long-lasting. Without continued application of an electric field, electroporated tissue often reverts back to its original condition. However, the duration of electroporation is dependent upon the degree of electroporation of the tissue. In other words, to obtain a longer term of electroporation, the term of applied voltage, or the amount of voltage applied, must be increased. Further, use of electroporation has, in some cases, been limited in the amount of ions and molecules that can be transported. This is particularly significant for larger transported species, such as macromolecules.

Therefore, a need exists for a new method for transferring fluids across tissue. In particular, a need exists for a method of modifying skin for transport of a material by electroporation.

SUMMARY OF THE INVENTION

The present invention relates to a new method of modifying epidermis for transport of a material by electroporation.

The method includes applying to epidermis an agent that, upon entry into the epidermis, will modify the epidermis to thereby cause an altered rate of transport of a material across the epidermis. The epidermis proximate to the agent is electroporated, whereby at least a portion of the agent enters the epidermis, thereby modifying the epidermis to cause an altered rate of transport of the material across the epidermis.

In one embodiment, the method further includes the step of applying the material to the epidermis, whereby the material is transported into the modified epidermis at a greater rate than into electroporated epidermis that is not modified by the agent. In another embodiment, the modifying agent can be employed to measure and monitor the condition or physiological changes in or beneath the modified epidermis.

The method of the invention has several advantages. For example, modification of tissue by the method of the invention can prolong the effects of electroporation, thereby enabling more transport and/or reduced application of voltage to administer a therapeutic treatment. Therefore, the amount of trauma endured by skin undergoing electroporation can be significantly diminished. Also, the amount of sensation, including pain suffered, as a consequence of applying electrical voltage to cause electroporation is typically reduced. Further, modification of epidermis by introduction of a modifying agent into the skin by electroporation can enable administration of other diagnostic treatments that would otherwise be difficult or impossible to perform. For example, the modifying agents themselves can be employed to measure or monitor physiological changes within or beneath the epidermis.

DETAILED DESCRIPTION OF THE INVENTION

The features and other details of the method of the invention will now be more particularly described and pointed out in the claims. It will be understood that the particular embodiments of the invention are shown by way of illustration and not as limitations of the invention. The principal features of this invention can be employed in various embodiments without departing from the scope of the invention.

Generally, electroporation is a method of increasing the permeability of tissue and cell membranes. The increased permeability allows transport, or migration, of chemical agents through the tissue or across cell membranes into cells. For example, electroporation can include applying a voltage across tissue in vitro to cause the permeability of the tissue and cell membranes of cells in the tissue to increase. If the tissue is in the presence of a suitable chemical agent, the chemical agent can then migrate across the tissue or into cells of the tissue. Electroporation has also been used to deliver drugs to tissue, in vivo, by applying electrodes to the surface of an organism and applying a voltage between the electrodes which exposes the tissue to an electric field. The tissue thereby becomes electroporated and allows delivery of a chemical agent, such as a drug, which has been applied either topically to the organism or injected into the blood stream of the organism, across the electroporated tissue and into cells of the electroporated tissue.

"Electroporation," as that term is used herein, means increased permeability of a cell membrane and/or at least a portion of cells of a targeted tissue to a chemical agent or other suitable material, wherein the increased permeability is caused by application of voltage across the cell or at least a portion of the tissue. An example of a suitable target tissue would be skin tissue, or epidermis, including the multilamellar bilayer membrane within the stratum corneum, and also envelopes of keratinocytes. The chemical agent can thereby migrate into or across the electroporated tissue and/or across the cell membrane and into the cell.

The method of the invention includes modifying epidermis for transport of material by electroporation. In particular, the method includes applying to epidermis an agent that, upon entry into the epidermis, will modify the epidermis to thereby cause an altered rate of transport of a material into the epidermis. The altered rate of transport can be an increased or decreased rate of transport, typically depending on the material being transported and/or the modifying agent employed with a particular material. The epidermis proximate to the modifying agent is electroporated, whereby at least a portion of the modifying agent enters the electroporated epidermis, thereby modifying the epidermis to cause an altered rate of transport of a material into the epidermis. It is to be understood that the modifying agent can be applied to the epidermis before, during or after electroporating the epidermis.

Examples of suitable apparatus for use with the method of the invention are disclosed in U.S. Ser. No. 07/705,778, filed May 28, 1991 and in U.S. Pat. No. 5,019,034; issued May 28, 1991, the teachings of which are incorporated by reference in their entirety. Other examples of suitable apparatus are described in the U.S. patent application entitled, *Apparatus and Method for Electroporating Tissue,* by Weaver et al., filed on Aug. 11, 1995, the teachings of which are incorporated by reference in their entirety. For example, electric pulses generated by suitable apparatus to cause electroporation by the method of the invention typically are exponential pulses having a time constant in about 3 milliseconds, but in some cases as long as about 300 milliseconds, and an amplitude in the range of between about 30 volts and about 500 volts, preferably between about 70 volts and about 200 volts. However, the pulse configuration can also be square, bipolar, etc. Generally, the number of pulses sufficient to cause electroporation is in the range of between about 1 and about 10, wherein the interval between pulses is in the range of between about 0.01 second and 1 minute. Usually the largest increase in permeability caused by electroporation occurs as a consequence of applying the first pulse.

Figure 1:
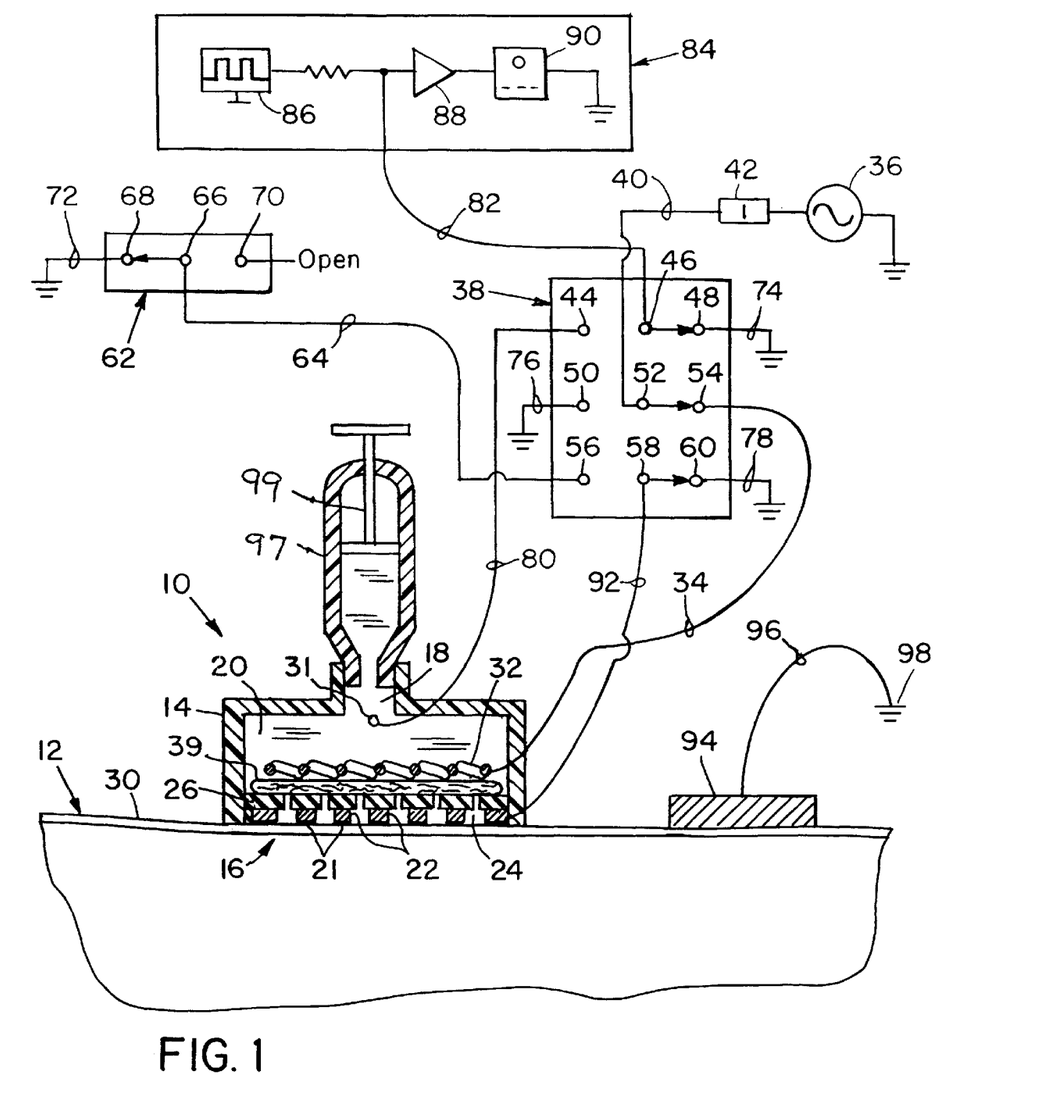
FIG. 1 is a schematic representation, shown partly in cross-section, of an apparatus suitable for conducting the method of the invention.

In one embodiment, the method of the invention can employ the apparatus represented in FIG. 1. However, other embodiments and methods can be employed, such as those described in U.S. Patent Application entitled "Apparatus and Method for Electroporation of Tissue", by James C. Weaver, Uwe Plignett and Timothy Vaughn, and filed on Aug. 9, 1996, the teachings of which are incorporated in their entirety. As shown in FIG. 1, electrode/reservoir device 10 is located at surface of epidermis 12. Electrode/reservoir device includes housing 14 that is suitable for containing composition 20, at least one component of which is to be administered to the patient. Perforate electrode plate 22 is located at application opening 16 within housing 14 and contacts epidermis 12. Perforate electrically-insulating sheet 26 is located above perforate electrode plate 22. Composition 20 contained within housing 14 is in fluid communication with epidermis 12 through aligned perforations 24 of perforate electrically-insulating sheet 26 and perforate electrode plate 22.

Electrode/reservoir device 10 causes the electric field to be mostly confined to the stratum corneum, i.e. minimal penetration of the electric field into the viable epidermal tissue adjacent the stratum corneum. Accordingly, the diameter of the hole(s) in first electrode 22 is generally chosen to be larger than the diameter of the hole(s) in electrically insulating layer 26. For example, if a 50 $\mu$m diameter hold is used in electrically insulating layer 26, the hole diameter in first electrode 22 can be about 80 $\mu$m, which provides an annular gap between the two holes of about 15 $\mu$m. Generally the width of the annular gap should be approximately equal to the thickness of the stratum corneum. Thus, for human skin with a stratum corneum thickness of about 20 $\mu$m, the width of the annular gap should be in a range of between about 1 $\mu$m and about 50 $\mu$m, preferably in a range of between about 5 $\mu$m and about 30 $\mu$m. The thickness of the electrically conducting layer comprising first electrode 22 can also be important. If layer 22 is not recessed into layer 26, then the thickness of layer 22 should be smaller than the thickness of the stratum corneum, i.e. smaller than about 20 $\mu$m. Specifically, unless first electrode 22 is recessed into layer 26, the thickness of layer 22 should be in a range of between about 10 nm ($10^{-8}$ m) and about 10 $\mu$m, and preferably in a range of between about 0.1 $\mu$m and about 1 $\mu$m. The lower bound for the thickness of first electrode 22 is determined primarily by an objective of having a low electrical resistance and of having a sufficient thickness of electrode material that the electrode is stable with respect to oxidation, electro-erosion and mechanical stress.

Electrode mesh 24 is located above perforate electrically-insulating sheet 20. Wire 34 extends from electrode mesh 24 to voltage source 36. An example of a suitable voltage source 36 is an exponential voltage pulse generator.

Switch 38 includes terminals 44, 46, 48, 50, 52, 54, 56, 58 and 60. Ground connections 74, 76, and 78 extend from terminals 48, 50, and 60, respectively.

Wire 80 extends from resistance-measurement electrode 31 to terminal 44 of switch 38. Wire 82 extends from terminal 46 of switch 38 to resistance device 84, which includes signal generator 86, amplifier 88, oscilloscope 90 and an electrical ground. Wire 92 extends from first electrode 22 to terminal 58 of switch 38.

Electrode 94 is located at epidermis 12 of the patient. Wire 96 extending from electrode 94 is connected to ground 98. Typically, electrode 94 is located between about five and about twenty centimeters from housing 14. It is to be understood the electrode 94 need not be employed to conduct the method of the invention.

The electrodes of electrode/reservoir device 10 are typically composed of a suitable conductive material, such as copper, gold, aluminum, etc., and also semiconducting materials such as silicon and germanium, and resistive materials such as carbon. Perforate electrically-insulated sheet 20 is formed of a suitable electrically nonconducting material, such as a suitable polyimide, etc. Housing 14 is typically composed of a suitable material, such as a suitable plastic or some other electrically non-conductive material. Generally, the diameter of perforations 24 at electrode 22 are larger than the diameter of perforations 24 at electrically-insulating layer 26, thereby providing an annular gap at the interface between first electrode 22 and electrically-insulating layer 26.

Figure 2:
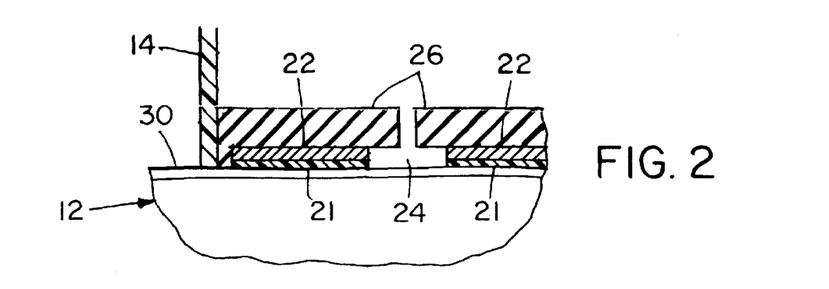
FIG. 2 is a cross section view of a portion of the apparatus shown in FIG. 1.

As can be seen in FIG. 2, at least a portion of the surface of perforate electrode 22 is provided with a coating of electrically insulating dielectric material 21, thereby providing an electrical capacitance. This capacitance serves the purpose of diminishing or preventing electrolysis at the aqueous solution/electrode interface and thereby reduces gas evolution and bubble formation within the electrode/ reservoir device. Such bubbles are generally undesirable, as their presence interferes with the flow of electrical currents along the intended pathways. Suitable materials for an electrically insulating dielectric coating include Teflon, Mylar, etc. and oxides such as aluminum oxide and tantalum oxide.

Composition within housing 14 is electrically conductive. Composition 20 typically includes at least one modifying agent that can enter or pass across epidermis while epidermis 12 is in an electroporated state, or a material that can be transported, by migration or some other mechanism, across epidermis that has been modified by the modifying agent. In one embodiment, composition 20 is a solution, wherein the agent and/or material are solutes of the solution. Examples of suitable solvents include physiological saline, phosphate buffered saline, distilled water with known trace electrolytes, etc. An electrically conductive gel or paste containing a modifying agent and/or other material to be directed into epidermis 12 by the method of the invention can also be employed as composition 20.

Returning to FIG. 1, the method of the invention includes applying at least one electrical pulse to epidermis 12 by applying a voltage between electrode mesh 24 and perforate electrode plate 18. A localized electric field is formed between electrode mesh 24 and perforate electrode plate 18 that extends within epidermis 12. The amplitude, number, and duration of pulses is sufficient to electroporate epidermis 12 proximate to perforate electrode plate 18. Typically, the epidermis is electroporated by applying a voltage from voltage source 36 in a range of between about 100 and about 250 volts. In one embodiment, the voltage is applied as a series of pulses. In a specific embodiment, the pulse-applied voltage has an average duration in a range of between about one millisecond and about three milliseconds per pulse, and the number of pulses employed to cause electroporation of epidermis 12 is in a range of between about one and about ten pulses.

There are two general modes of use for the electrode/ reservoir device 10, an electrical pulsing mode or a resistance measurement mode, with the pulse/measurement choice implemented by using switch 38. As shown in FIG. 1, switch 38 is set in the "pulsing mode," such that a voltage pulse produced by pulse generator 36 results in electrical current flow through wire 40, which passes through current sampling resistor 42 and flows to terminal 52 of switch 38, and then (in the position shown) reaches terminal 54 of switch 38, which is connected by wire 34 to conduct the current into electrode/reservoir device 10 to reach second electrode 32, and then passes through electrically conducting fluid (composition) 20, through filter 100, through one or more holes in electrically insulating layer 26, and then into and through epidermis 12, where the current spreads out and reaches perforate electrode 22, with the current exiting electrode/reservoir device 10 along wire 92 to reach terminal 58 of switch 38, and then to terminal 60 of switch 38, which is connected to ground that provides a return path to pulse generator 36. During such pulsing the skin resistance measurement system 84 is connected by wire 82 to terminal 46 of switch 38, and then in the switch position shown, connected to terminal 48, which is connected to ground 74, with this grounding of measurement system 84 serving to protect said measurement system from stray currents and capacitive pickup during pulsing.

During measurements carried out before or after pulsing, two different measurement modes can be used, one without the use of separate electrode 94, and one which involves electrode 94. For the switch position shown for measurement mode selection switch 62, separate electrode 94 is not involved. In this mode, a small resistance measurement current, for example a small amplitude square wave current (as indicated in resistance measurement device 84), flows from resistance-measurement device 84 through wire 82 to terminal 46 of switch 38, then to terminal 44 of switch 38 through wire 80 into electrode/reservoir device 10 to resistance-measurement electrode 31, through electrically conducting fluid (composition) 20, through one or more holes in electrically insulating layer 26, and then into and through epidermis 12, where the current spreads out and reaches perforate electrode 22, then through wire 92 to terminal 58 of switch 38, which is now connected to terminal 56 of switch 38, then through wire 64 to terminal 66 of measurement mode selection switch 62, which in the position shown is connected to terminal 68 of switch 62, and then through wire 72 to ground, thereby completing the measurement circuit to the ground of resistance-measurement device 84. Note that in this resistance-measurement mode separate electrode 94 is usually not present.

In the alternative resistance-measurement mode, resistance-measurement selection switch 62 is put into a second position (not shown). With this setting, the resistance-measurement device measurement current cannot flow out of electrode/reservoir device 10 along wire 92 and into switch 62 to reach ground, because switch 62 is connected to terminal 70, which is electrically open (a very high resistance). Thus, resistance-measurement device measurement current instead flows across the epidermis at the site of one or more holes in perforate electrode 22, but in this case more deeply into the epidermal tissue but with significant current spreading, with the current within the epidermal tissue reaching electrode 94 (electrode area 48 is generally much larger than the total area of the holes in perforate electrode 22), and then through wire 96 to ground 98. In this alternative resistance-measurement mode the resistance-measurement current flows through and within the epidermis at two distinct sites: at the electrode/reservoir device 10 and at the separate electrode 94, but only the resistance of the epidermis adjacent electrode/reservoir device 10 is usually altered by pulsing, and this means that the resistance measurement involving the two sites can be used to infer the resistance changes at the site of the electrode/reservoir device 10.

Although the method of the invention is not to be bound by any particular theory, it is believed that the electroporated portion of epidermis 12 includes stratum corneum layer 54 of epidermis 12. It is also believed that electroporation of epidermis 12 includes temporary disruption of lipid-containing barriers of epidermis 12, thereby causing the formation of aqueous pathways through the lipid-containing barriers, such as multi-lamellar lipid regions of stratum corneum 30 of epidermis 12. The degree or amount of electroporation can be measured following application of electrical pulses by conducting a measurement of electrical resistance across epidermis 12. The measurement of electrical resistance can be obtained by activating electrical resistance measurement device 84. Typically, the degree or amount of electroporation can be indirectly determined as being inversely proportional to the electrical resistance of epidermis 12.

Electroporation of epidermis 12 causes a modifying agent component of composition 20 to migrate from within housing 14 and into or across epidermis 12. Suitable modifying agents are those which can enter or pass across epidermis 12 while epidermis 12 is in an electroporated state, and which thereby modify the properties of epidermis 12 for subsequent therapeutic or diagnostic treatment. For example, the modifying agent can be a chemical compound or particulate material, such as a bead, that can be employed as an indicator of a physiological condition or change within a patient. Modifying agents that are beads, for example, can include or contain at least one drug that is released from the bead into or beneath epidermis 12. Typically, suitable beads have a diameter in a range of between about 0.01 and about thirty micrometers. Preferably, the beads have a diameter in a range of between about 0.1 and about one micrometer.

Introduction of material by the combined effect of mechanical deformations of skin and electroporation can also be used. For example, placement of electrodes that move slightly during application of an electrical pulse can mechanically deform the skin tissue, thereby altering aqueous pathways created by electroporation. Further, such relative motion between electrodes and skin tissue can create pressure differences which contribute to the transport of material into or across the skin tissue. This aspect of the invention is very general, as it is not limited to skin tissue. That is, similar electromechanical deformation can be used with tumor tissue for altered transport of material into, or out of, tumor tissue. Other tissues such as normal liver tissue, kidney tissue, etc. can also be used. In a specific example, if the electrodes are not positioned relative to each other by rigid material, but instead are separated by tissue, then even the process of applying an electroporating voltage across the tissue can result in electrocompression. This squeezing of tissue is due to the electrical permittivity of tissue and the mechanical deformability of tissue.

In another embodiment, particles of modifying agents can cause a formation of, or maintain, aqueous pathways within epidermis 12 and/or a region of tissue beneath epidermis 12, such as a tumor. The aqueous pathways can then be employed as means for exit of fluids from within the tumor, thereby reducing pressure within the tumor. Optionally, pressure can be applied to the tumor by a suitable mechanical means, such as by application of an ultrasound treatment. Also, negative pressure, or suction, can be applied to the tumor by suitable means. Composition 20 can be pressurized by a suitable method, such as by applying pressure to syringe 97 at inlet 18 of housing 14. Alternatively, fluids can be withdrawn from a patient through an electroporated region into housing 14 by withdrawing a plunger 99 of syringe 97, i.e. by applying negative pressure (suction), or by applying an electrical driving force in the outward direction, e.g., by probes of suitable polarity.

In another embodiment, the modifying agent can include at least one type of optical bead. For example, the optical beads can be a combination of an optical standard bead and an optical indicator bead. The optical standard bead provides a suitable reference characteristic, such as a standard fluorescent measurement, and the optical indicator bead is responsive to a physiological change in its environment, such as a change in pH, glucose, etc. A suitable measurement of a physiological condition or change can be measured or monitored by measuring the change in the optical indicator bead and/or a difference between the optical indicator bead and the optical standard bead. For example, beads containing fluorescein molecules on their surface have green fluorescence emission that is responsive to pH changes in the physiological range around pH 7.4, while beads provided with sulforhodamine have red fluorescence emission that is relatively pH insensitive. Other examples of suitable optical indicator beads are those that are responsive to environmental conditions selected from a group consisting of oxygen partial pressure, carbon dioxide partial pressure, pH and temperature. In one embodiment, the particles are suitable for conducting a glucose assay, or for an assay of a suitable physiological electrolyte.

In still another embodiment, the modifying agent can carry an electrical change. Optionally, the modifying agent can be a reducing agent, such as sodium thiosulfate or glutathione. Alternatively, the modifying agent can be an oxidizing agent or a denaturing agent. The modifying agent can be an enzyme that catalyzes a reaction that disrupts a barrier of epidermis 12. In still another embodiment, the modifying agent can modify epidermis 12 by physicochemically disrupting a keratin component of epidermis 12. Examples of modifying agents that carry electrical charges are anions, such as heparin, and polystyrene beads with surface carboxylate groups. In still another embodiment, beads employed as modifying agents can be suitable for measuring transmission of light through portions of the epidermis containing the beads.

The modifying agent can be suitable for increasing the rate at which a material can migrate into and/or across epidermis 12. Examples of suitable agents for modifying the epidermis to increase the rate of migration include suitable reducing agents, enzymes and electrically charged chemicals or particles and/or agents that modify epidermis 12 by physiochemically disrupting the keratin component of the epidermis 12. Examples of suitable agents for decreasing the rate of migration include charged molecules, and denaturing agents that swell the keratin matrix within corneocytes of the stratum corneum. In another embodiment, the modifying agent can increase the rate at which a material migrates into or across epidermis 12 by creating pathways within or through the epidermis. An example of a suitable modifying agent for creating such pathways includes particles, such as beads. Formation of pathways by introduction of particles into or through the epidermis can be facilitated by applying a force to the particles, thereby facilitating their transport through the electroporated epidermis. An example of a suitable force is a mechanical force or an electromagnetic force, such as magnetism.

In one embodiment, the material to be introduced into or through epidermis 12 is a component of composition 20 within housing 14. Alternatively, the material can be applied to epidermis 12 before or after electroporation of epidermis 12. Also, it is to be understood that material can be applied to epidermis 12 before, during or after introduction of the modifying agent into epidermis. Examples of suitable materials for introduction into epidermis by the method of the invention include proteins, nucleic acids and particles. Other materials can include inactivated microorganisms, such as inactivated viruses, bacteria, etc., that can be introduced into tissue for the purpose of immunization. An example of a suitable particle is a bead, such as a bead that includes at least one drug that can diffuse from the bead subsequent to introduction into epidermis 12. Suitable beads can have a diameter in a range of between about 0.01 micrometers and about thirty micrometers, for example. Preferably the beads have a diameter in a range of between about 0.1 micrometers and about one micrometer.

The material is transported into or across the modified epidermis by a mechanism, such as active transport or diffusion, at a rate that is greater than that which would occur into or through unmodified epidermis. Optionally, the rate of transport of the material into or through epidermis 12 can be further facilitated by application of a suitable force. An example of a suitable force is a mechanical force, such as hydrostatic pressure, osmotic pressure or compression associated with squeezing of the epidermis by motion of the electrodes relative to the tissue.

In one specific embodiment, a mechanical force can be applied by pressurizing a composition that includes the material within housing. The composition can be pressurized by a suitable method, such as by applying pressure to syringe 97 at said housing 14. Alternatively, fluids and particles can be withdrawn, i.e. extracted from a patient through an electroporated region into housing 14 by withdrawing a plunger 99 of syringe 97, i.e. by applying a negative pressure (suction).

In another embodiment, transport of the material into or across modified epidermis can be facilitated by application of an electric field across the modified epidermis, whereby the rate of iontophoretic transport of the material across the epidermis 12 is increased.

Although it is generally preferred to use the apparatus of this invention with pulses in the range of about 50 volt to about 500 volt, because such pulses cause electroporation within the stratum corneum, and result in the largest molecular transport, the apparatus can also be used with pulse in the range of about 5 volt to about 50 volt, because pulses in this range predominantly cause electroporation of the linings of sweat gland ducts.

The invention will now be further and specifically described by the following examples. All parts and percentages are by weight unless otherwise specified.
Exemplification

EXAMPLE 1

This invention was illustrated by a number of experiments that introduced different concentrations of a reducing agent into skin, and measuring the fluxes of the protein lactalbumin and a smaller charged molecule, sulforhodamine.

FITC-lactalbumin (mw≈15 kDa, charge≈−15) was obtained from Molecular Probes Inc., Eugene, Oreg.; sodium thiosulfate (mw=158 Da, charge of anion is −2) and sulforhodamine (mw=602 Da, charge=−1) were obtained from Sigma Chemical Co., St. Louis, Mo. The lactalbumin was purified using a Centriprep Concentrator 3 (3000 MW cutoff) centrifugal dialysis device (Amicon Division, W. R. Grace and Co., Beverly, Mass.). The fluorescence of the final dialysate (presumably due to a combination of low molecular weight molecules and FITC-lactalbumin which had passed through the membrane) was significantly less than the fluorescence observed in the receptor compartments in all experiments in which we observed a significant flux.

The phosphate buffered saline (PBS) solutions with reducing agent were adjusted to pH 7.4 (with KOH) before adding the FITC-lactalbumin. There is a fast (less than 1 second for completion) reaction between thiosulfate and fluorescein. A 35% reduction in fluorescence is seen at 200 mM thiosulfate, and about 80% at 1M thiosulfate. We normalized the amount of fluorescence signal we observe in the receptor compartment to correct for this effect.
Skin Preparation Heat-stripped stratum corneum was used in all experiments (area exposed to the electrical field=0.7 cm$^2$) (Prausnitz et al., PNAS, v. 90, p. 10504–10508, 1993). The skin was obtained from the abdomen, arm, or back of adult human cadavers. Prior to heat-stripping the skin was stored at −70° C. for one to six months. After heat-stripping, the skin was stored at 4° C. in a 95% humidity environment.
Pulse application and electrical measurements As in previous studies (see Prausnitz et al., ibid) high-voltage pulses were delivered using an exponential pulser (Electroporation System 600, BTX Industries, San Diego, Calif.) modified for automated control. The electrode design, orientation and permeation chambers have been described previously. The pulse time constant $\tau_{pulse}$ was 1.0 ms (using 50Ω internal shunt resistance) with 0.1 ms variation during an experiment. The transdermal voltage is much less than the pulsing voltage because there is a voltage divider effect involving the bathing solution, electrodes, and skin. Voltage traces were acquired and stored on a Hewlett-Packard 54601 digital oscilloscope, and passive electrical properties were calculated as described by Pliquett, U., Langer, R., and Weaver, J. C., "The Change in the Passive Electrical Properties of Skin due to Electroporation," *Biochem. Biophys. Acta*, 1239, 111–121 (1995). The resistance of the skin prior to pulsing was greater than 60 kΩ for all experiments (skin area of about 0.7 cm$^2$).
Image acquisition A biocular fluorescence microscope (Olympus BH-2) was used, together with an Olympus OM2 camera. Shutter times were between ¼ and 3s. Confocal images were acquired through a BioRad—Laser Scanning Device attached to a Zeiss Axioplan microscope and displayed using a PC. The lipid structures of the skin were stained with a 0.1 mM solution of Nile Red (Sigma Chemical Co.) for 30 minutes to prior to confocal imaging.
Fluorescent molecule transport across the stratum corneum The concentrations of lactalbumin and sulforhodamine in the donor compartment were 0.1 mM each. The concentration of reducing agent was 0.1, 0.2 or 1.0M. The fluorescence of the receptor compartment solution was measured using a spectrofluorimeter (Fluorolog 2, model F112AI, SPEX Industries, Edison, N.J.).
RESULTS The goal of this example was to reduce the disulfide linkages of the keratin matrix within the stratum corneum. The disulfide linkages are formed between cysteine residues from adjacent polypeptide chains and give the keratin matrix much of its tensile strength. These crosslinks may also act as a sieve for the transport of larger molecules (see Edwards et al., J. Controlled Release, v. 34, p. 211, 1995). Thus, the matrix may be made more permeable to large molecules (>1000 mw) such peptides, proteins, carbohydrates, and polynucleotides (e.g. DNA) after a reducing agent has been electroporated into the stratum corneum. Thiosulfate is a powerful reducing agent which is used to rapidly reduce (on the order of minutes) disulfide bonds for denaturing electrophoresis.

A rough estimate of the amount of keratin in a wet matrix is 0.1 by weight. An order of magnitude estimate of the sulfur in cysteine as a percentage of total keratin weight is 0.01. One can then estimate the molarity of disulfide crosslinks to be 15 mM; therefore, a concentration of 30 mM of reducing agent would be needed to fully reduce the matrix. Of course, full reduction may not be needed to significantly increase transport of large molecules through this matrix.

The passive (i.e. no pulsing) lactalbumin flux was measured and found to be the same order of magnitude as the flux without pulsing without reducing agents. In contrast, the sulforhodamine flux exhibited a significant increase with pulsing in the absence of reducing agents. However, by introducing the reducing agent, significant lactalbumin transport occurs during and after pulsing.

The electrical resistance of the reduced skin post pulse is the same as that of the pulsed-only skin, 2 k$\Omega$. This result argues against aqueous pathways being created by the reducing agent alone.

Fluorescence microscopy revealed that FITC-lactalbumin was localized to areas 10–30 $\mu$m in diameter in the skin. Further, FITC-lactalbumin was observed to penetrate all of the keratinocyte layers of the stratum corneum. FITC-lactalbumin fluorescence was always located in the area of the heat-stripped skin corresponding to the dermal papillae (troughs of the epidermis) and no localized regions of staining appeared in the Rete pegs (crests of the epidermis). Significantly, there was little or no fluorescence in the skin appendages (hair follicles and sweat ducts).

DISCUSSION

The observation of fluorescence in all layers of the stratum corneum by stereomicroscopy is direct evidence that the combination of electroporation and reducing agents creates localized transport regions (LTR's) across the skin for a macromolecule such as lactalbumin. LTR's do not correspond to appendages. These results are in accord with what has been seen for the transport of smaller, negatively charged molecules calcein and sulforhodamine across the skin (See Pliquett et al., "Imaging of Fluorescent Molecules and Small Ion Transport Through Human Stratum Corneum During High-Voltage Pulsing: Localized Transport Regions are Involved" *J. Biophys. Chem.* 58:185–204, 1996) and highly charged oligonucleotides without reducing agents (see Zewert et al., BBRC, v. 212, p. 286–292, 1995). In summary, a significant flux of lactalbumin was not observed with electroporation alone, and instead occurred only when electroporation was used in combination with sodium thiosulfate.

Flux measurements were determined by relative fluorescence of donor compartment aliquots. As shown in Tables 1-1, 1-2, and 1-3, as was found in many other experiments with short ($\tau_{pulse} \approx 1$ ms) pulses, a small or insignificant lactalbumin flux occurred for pulsing for one hour every five seconds at an electrode voltage of 1,000 V (maximum pulse voltage across the electrodes) if no thiosulfate was present. However, if thiosulfate is provided, there is a dose-response behavior in which significantly larger lactalbumin fluxes occur for pulsed skin, with the higher thiosulfate concentrations correlating with larger lactalbumin fluxes.

A striking observation was made: for the higher thiosulfate concentrations, pulsed skin often exhibited small (~10–20 micron diameter) holes that were visualized by microscopy (Tables 1-1, 1-2, 1-3). The data are presented in arbitrary fluorescent units, which provide relative values of the concentrations of fluorescent and fluorescent-labelled molecules in the aliquots taken from the donor compartment. Table 1-3 compares the effect of the modifying agent sodium thiosulfate to a sodium chloride solution with the equivalent electrical conductivity, which shows that the modifying agent causes significant alteration of both lactalbumin and sulforhodamine. Our present interpretation is that electroporation in the presence of the higher concentrations of thiosulfate leads to a higher rate of hole formation, by disrupting the keratin matrix within the corneocytes of a stack of about 15 corneocytes across the stratum corneum, such that the entire stack is disrupted, and that such holes are a striking example of skin modification due to the combination of this type of electrical pulsing and thiosulfate.

Table 1-4 summarizes a single, similar experiment with glutathione at 0.2M. In this case the effect is much smaller, with an approximately threefold increase in lactalbumin flux during the one hour of pulsing, and a much larger increase in sulforhodamine flux.

TABLE 1-1

| Donor Solution: Conditions: | | | Electroporation | | |
|---|---|---|---|---|---|
| Thiosulfate 0.2M Lactalbumin 0.1 mM sulforhodamine 0.1 mM | | | (1000 V - 1 ms) 1/5 sec 1 h | | |
| | thio .2M 1 | thio .2M 2 | thio .2M 3 | thio .2M 4 | control 1 | control 2 |
| piece of skin | 1 | 2 | 2 | 2 | 1 | 2 |
| R skin before electroporation | 140 k$\Omega$ | 100 k$\Omega$ | 200 k$\Omega$ | 80 k$\Omega$ | 90 k$\Omega$ | 90 k$\Omega$ |
| fluxes (relative fluorescence unit) before pulsing | not observed | 2.7 e3 lact 2.9 e3 sulfo | 5.4 e3 3.0 e3 | 2.4 e3 5.6 e3 | not observed | 2.4 e3 6.4 e3 |
| pulsing | 1.8 e5 4.7 e5 | 1.7 e4 2.5 e5 | 5.7 e6 7.2 e6 | 1.8 e5 6.3 e5 | 1.3 e4 7.5 e4 | 5.2 e3 4.9 e5 |
| 1 h after p | 2.5 e4 2.8 e5 | 1.0 e4 1.7 e5 | 2.7 e6 4.1 e6 | 3.8 e6 5.0 e6 | 2.8 e3 5.8 e4 | 2.8 e3 1.8 e5 |

TABLE 1-1-continued

| | | | | | | |
|---|---|---|---|---|---|---|
| 2 h after p | 5.6 e3 | 5.2 e3 | 3.8 e6 | 1.3 e6 | 2.5 e3 | 3.4 e3 |
| | 1.2 e5 | 3.8 e4 | 5.3 e6 | 2.1 e6 | 3.2 e4 | 4.8 e4 |
| 3 h after p | 4.2 e3 | 3.9 e3 | 3.1 e5 | 3.1 e6 | 3.0 e3 | 2.7 e3 |
| | 7.5 e4 | 2.0 e4 | 9.3 e5 | 4.3 e6 | 2.3 e4 | 3.1 e4 |
| microscopy | not observed | 1 hole day after: 1 hole | ~15 holes day after: ~15 holes | 2 holes day after: 3 holes | not observed | no hole |

Notation and Abbreviations
lact = lactalbumin (top entry in each part of the table)
sulfo = sulforhodamine (bottom entry in each part of the table)
thio = thiosulfate
$2.7e^3 = 2.7 \times 10^3$ (example of numerical notation)
after p = after pulsing
$R_{skin}$ = transdermal electrical resistance

TABLE 1-2

| Donor Solution: Thiosulfate 0.1 or 1M Lactalbumin 0.1 mM sulforhodamine 0.1 mM | | Electroporation Conditions: (1000 V - 1 ms) 1/5 sec 1 h | |
|---|---|---|---|
| | thio 0.1M | control | thio 1M | control |

| | thio 0.1M | control | thio 1M | control |
|---|---|---|---|---|
| piece of skin | 1 | 1 | 1 | 1 |
| R skin before electroporation | 600 kΩ | 600 kΩ | 100 kΩ | 80 kΩ |
| fluxes (fluoresc) before pulsing | 6.8 e3 lact 1.8 e4 sulfo | not observed | not observed | not observed |
| pulsing | 6.6 e3 lact 1.0 e5 sulfo | 1.2 e4 1.1 e5 | 3.7 e6 2.5 e6 | 3.8 e3 1.1 e5 |
| 1 h after p | + 1 h 30 pulsing 8.0 e3 6.4 e4 | + 1 h 30 pulsing 1.8 e4 3.2 e4 | 1.3 e6 1.4 e6 | 2.6 e3 5.0 e4 |
| 2 h after p | not observed | not observed | 3.0 e6 2.2 e6 | 2.4 e3 2.5 e4 |
| 3 h after p | not observed | not observed | not observed | not observed |
| microscopy | not observed | not observed | several holes | no hole |

Notation and Abbreviations
fluoresc = fluorescence

TABLE 1-3

| Donor Solution: Thiosulfate 0.2 1M or NaCl 0.4M Lactalbumin 0.1 mM sulforhodamine 0.1 mM | | Electroporation Conditions: (1000 V - 1 ms) 1/5 sec 1 h | |
|---|---|---|---|

| | thio 0.2M | NaCl 0.4M |
|---|---|---|
| piece of skin | 2 | 2 |
| R skin before electroporation | 110 kΩ | 110 kΩ |
| fluxes (fluoresc) before pulsing | 2.1 e3 lact 3.4 e3 sulfo | 2.0 e3 2.1 e3 |
| pulsing | 6.6 e3 3.1 e5 | 1.0 e4 3.6 e5 |
| 1 h after p | 5.0 e4 3.0 e5 | 3.0 e3 1.9 e5 |
| 2 h after p | 6.5 e4 1.5 e5 | 4.3 e3 4.7 e4 |
| 3 h after p | 1.4 e4 8.8 e4 | 3.4 e3 2.7 e4 |
| microscopy | 2 holes | no hole |

TABLE 1-4

| Donor Solution: Glutathione 0.2M Lactalbumin 0.1 mM sulforhodamine 0.1 mM | Electroporation Conditions: (1000 V - 1 ms) 1/5 sec 1 h |
|---|---|

| | glutathione 0.2M |
|---|---|
| piece of skin | 1 |
| R skin before electroporation | 70 kΩ |
| fluxes (fluoresc) before pulsing | 4.9 e3 lact 4.4 e3 sulfo |
| pulsing | 1.8 e4 3.3 e5 |
| 1 h after p | 5.2 e3 2.0 e5 |
| 2 h after p | 5.1 e3 8.4 e4 |
| 3 h after p | 5.3 e3 6.4 e4 |
| microscopy | no holes |

TABLE 1-5

Calibration Curve lactalbumin/sulforhodamine

| donor solution | lactalbumin | sulforhodamine |
|---|---|---|
| dilution 10 fold | 7.8 e6 | 1.2 e7 |
| dilution $10^2$ fold | 3.7 e6 | 3.5 e6 |
| dilution $10^3$ fold | 3.5 e5 | 2.4 e5 |
| dilution $10^4$ fold | 3.2 e4 | 1.7 e4 |
| dilution $10^5$ fold | 6.0 e3 | 3.6 e3 |
| dilution $10^6$ fold | 2.6 e3 | 1.9 e3 |
| PBS | 2.4 e3 | 1.9 e3 |
| nothing | 1.5 e3 | 1.5 e3 |

EXAMPLE 2

This invention was also attempted by experiments that introduced an oxidizing agent into skin, and measured the fluxes of two charged molecules, calcein and sulforhodamine.

Calcein (mw=623 Da, charge=−4) was obtained from Molecular Probes Inc., Eugene, Oreg.; sulforhodamine (mw=602 Da, charge=−1) and sodium periodate ($NaIO_4$, mw=213.9 Da) were obtained from Sigma Chemical Co., St. Louis, Mo.

The fluorescence of both calcein and sulforhodamine was greatly diminished by the oxidizing agent. Therefore, measurement of the calcein and sulforhodamine transport measured immediately after pulsing gives completely misleading results. For this reason the donor compartment contents were replaced after pulsing with saline containing only the calcein and sulforhodamine, and this allowed measurement of calcein and sulforhodamine fluxes of skin modified by introduction of sodium periodate by electroporation.

Skin preparation

Heat-stripped stratum corneum was used in all experiments (area exposed to the electrical field=0.7 cm$^2$) [Prausnitz et al., PNAS, v. 90, p. 10504–10508, 1993]. The skin was obtained from the abdomen, arm, or back of adult human cadavers. Prior to heat-stripping the skin was stored at −70° C. for one to six months. After heat-stripping, the skin was stored at 4° C. in a 95% humidity environment.

Two pieces of skin were used: one with oxidizing agent, one as a control. As described by Prausnitz et al. [ibid], measurement of the receptor compartment concentration was carried out by taking aliquots and measuring the solution fluorescence in a spectrofluorimeter. The donor solution contained 1 mM calcein, 1 mM sulforhodamine and 1M NaIO$_4$. (The control (no pulsing) omitted the NaIO$_4$.) The pulsing protocol was 1 hour passive diffusion, 1 hour of pulsing with one 1000-V, 1-ms time constant pulse every 5 seconds. The temperature of the solution was 25° C.

Pulse application and electrical measurements

As in previous studies (see Prausnitz et al., ibid) high-voltage pulses were delivered using an exponential pulser (Electroporation System 600, BTX Industries, San Diego, Calif.) modified for automated control. The electrode design, orientation and permeation chambers have been described previously. The transdermal voltage is much less than the pulsing voltage because there is a voltage divider effect involving the bathing solution, electrodes, and skin. Voltage traces were acquired and stored on a Hewlett-Packard 54601 digital oscilloscope, and passive electrical properties were calculated. The resistance of the skin prior to pulsing was greater than 60 kΩ for all experiments.

Image acquisition

A biocular fluorescence microscope (Olympus BH-2) was used, together with an Olympus OM2 camera. Shutter times were between ¼ and 3s. Confocal images were acquired through a BioRad—Laser Scanning Device attached to a Zeiss Axioplan microscope and displayed using a PC. The lipid structures of the skin were stained with a 0.1 mM solution of Nile Red (Sigma Chemical Co.) for 30 minutes to prior to confocal imaging.

Fluorescent molecule transport across the stratum corneum

The concentrations of calcein and sulforhodamine in the donor compartment were 1 mM each. The fluorescence of the calcein and sulforhodamine in the receptor compartment solution was measured using a spectrofluorimeter (Fluorolog 2, model F112AI, SPEX Industries, Edison, N.J.). The relative values of fluorescence for the same time intervals can be used, with a correction for background, to determine the relative fluxes for pulsing.

RESULTS

The goal of this example was to disrupt the keratin matrix within the stratum corneum by the use of an oxidizing agent rather than a reducing agent. The results of two different experiments are shown below in Tables 2-1 and 2-2.

TABLE 2-1

| fluxes | molecule | passive (not pulsed, no NaIO$_4$) | control (pulsed, no NaIO$_4$) | experiment (pulsed, NaIO$_4$) |
|---|---|---|---|---|
| passive (1 h) (after pulsing) | ca | 2.2 e3 | 2.5 e3 | 7.4 e3 |
| | sr | 8.7 e3 | 2.4 e3 | 2.8 e4 |

TABLE 2-2

| fluxes | molecule | control (pulsed, no NaIO$_4$) | experiment (pulsed, NaIO$_4$) |
|---|---|---|---|
| passive (1 h) (before pulsing) | ca | 5.5 e4 | 1.2 e4 |
| | sr | 5.8 e4 | 5.1 e4 |
| passive (1 h) (after pulsing) | ca | 2.3 e5 | 2.9 e4 |
| | sr | 5.8 e4 | 9.1 e3 |

These oxidizing agent experiments did not cause a significant, understandable alteration of molecular transport. Fluorescence microscopy revealed that very large localized transport regions (~1.2 mm diameter) occur in the periodate-exposed pulsed skin, but not the control (non-periodate-exposed, pulsed) skin.

Significantly, there was little or no fluorescence in the skin appendages (hair follicles and sweat ducts). Overall, these experiments were not conclusive.

EXAMPLE 3

This invention was further illustrated by a series of experiments that introduced charged molecules into the skin in order to modify aqueous pathways such that the transport of other molecules was altered. Here our hypothesis was that charge within aqueous pathways prevents shrinkage and closure of aqueous pathways, thereby modifying transport. Further, transport of highly charged molecules may be inhibited within aqueous pathways which stay open, due to electrostatic repulsion.

Both molecular flux and skin electrical resistance measurements were made. The agent for modifying the skin by occupying aqueous pathways was the highly charged molecule heparin (Sigma Chemical Co., St. Louis, Mo.).

Skin preparation

Heat-stripped stratum corneum was used in all experiments (area exposed to the electrical field=0.7 cm$^2$) [Prausnitz et al., PNAS, v. 90, p. 10504–10508, 1993]. The skin was obtained from the abdomen, arm, or back of adult human cadavers. Prior to heat-stripping the skin was stored at −70° C. for one to six months. After heat-stripping, the skin was stored at 4° C. in a 95% humidity environment.

Pulse application and electrical measurements

As in previous studies (see Prausnitz et al., ibid) high-voltage pulses were delivered at 5-second intervals for 1 hour, using an exponential pulser (Electroporation System 600, BTX Industries, San Diego, Calif.) modified for automated control. The electrode design, orientation and permeation chambers have been generally described previously, but here the additional feature of providing an agarose gel (1 cm thick) between stainless steel rod electrodes (2 mm diameter) was used to prevent electrochemical reaction byproducts from reacting with the calcein and sulforhodamine. The pulse time constant $\tau_{pulse}$ was 1.0 ms with 0.1 ms variation during an experiment. The transdermal voltage is much less than the pulsing voltage because there is a voltage divider effect involving the bathing solution, electrodes, and skin. Voltage traces were acquired and stored on a Hewlett-Packard 54601 digital oscilloscope, and passive electrical properties were calculated as described by Pliquett U., Langer, R., and Weaver, J. C., "The Change in the Passive Electrical Properties of Skin due to Electroporation" *Biochem. Biophys.* Acta 1239, 111–121, (1995). The resistance of the skin prior to pulsing was greater than 60 kΩ for all experiments. The temperature was controlled to be 37° C.

Image acquisition

A biocular fluorescence microscope (Olympus BH-2) was used, together with an Olympus OM2 camera. Shutter times were between ¼ and 3s.

Fluorescent molecule transport across the stratum corneum

The concentrations of calcein and sulforhodamine in the donor compartment were 1 mM each. The concentration of heparin was as noted in Tables 3-1 and 3-2. The fluorescence of aliquots from the receptor compartment solution was measured using a spectrofluorimeter (Fluorolog 2, model F112AI, SPEX Industries, Edison, N.J.).

RESULTS

The goal of this example was to introduce electrical charge into aqueous pathways such that transport of other molecular species would be modified.

The fluxes of calcein and sulforhodamine in Table 3-1 were calculated in units of $\mu g\ cm^{-2}\ hr^{-1}$, instead of providing only the donor aliquot fluorescence. A significant effect on calcein flux of introducing heparin is seen by comparing the zero heparin and 200 mg/ml heparin results for both $\tau_{pulse}=1$ ms and 2 ms. For $\tau_{pulse}=2$ ms, the calcein flux is decreased by a factor of $17/4.9\approx3.5$ during the 1 hour of pulsing, with a similar decrease in cumulative transport over the 1 hour pulsing followed by 9 hours passive transport. At the same time, the sulforhodamine (and cumulative 10-hour transport) increased, by a factor of about 2.

For $\tau_{pulse}=1$ ms, similar decreases in calcein were observed, with a dose-response relationship in which larger heparin concentrations decreased calcein transport, and increased sulforhodamine transport.

TABLE 3-1

| | calcein | | sulforhodamine | |
|---|---|---|---|---|
| | max flux ($\mu$m/cm2 · h) | cumulative calcein transported after 10 h ($\mu$m/cm$^2$) | max flux ($\mu$m/cm2 · h) | cumulative sulforhodamine transported after 10 h ($\mu$g/cm2) |
| 1000 V – 2 ms no heparin | 17 | 17.5 | 15.5 | 18.5 |
| 1000 V – 2 ms hep 200 mg/ml | 4.9 | 5 | 26 | 34 |
| 1000 V – 1 ms no hep | 11.5 | 13 | 10 | 15.5 |
| 1000 V – 1 ms hep 200 mg/ml | 2.5 | 3.5 | 16.5 | 25 |
| 1000 V – 1 ms hep 10 mg/ml | 3.4 | 4.1 | 5.8 | 7.3 |
| 1000 V – 1 ms hep 1 mg/ml | 7.8 | 9 | 8.5 | 11 |
| 1000 V – 1 ms hep 0.1 mg/ml | 11.8 | 13 | 11 | 13 |

TABLE 3-2

| | calcein | sulforhodamine |
|---|---|---|
| | slope of the rising part of the curve "flux versus time" (cps/second) | |
| 1000 V – 2 ms no heparin | 1400 | 660 |
| 1000 V – 2 ms hep 200 mg/ml | 350 | 2030 |
| 1000 V – 1 ms no hep | 1200 | 210 |
| 1000 V – 1 ms hep 200 mg/ml | 100 | 760 |
| 1000 V – 1 ms hep 10 mg/ml | 130 | 240 |
| 1000 V – 1 ms hep 1 mg/ml | 550 | 360 |
| 1000 V – 1 ms hep 0.1 mg/ml | 1330 | 410 |

EXAMPLE 4

This invention was illustrated by experiments that introduced a reducing agent (sodium thiosulfate) into skin so that small, charged beads could be transported across the skin.

Fluorescent polystyrene beads (0.2–2 micron diameter; charge $\approx -10^6$ to $10^7$) were obtained from Bangs Laboratories [Carmel, Ind.] and sodium thiosulfate (mw=158 Da, charge of anion is –2) was obtained from Sigma Chemical Co., St. Louis, Mo. The sodium thiosulfate was applied adjacent to the stratum corneum side of the skin at 1M.

The phosphate buffered saline (PBS) solutions with reducing agent were adjusted to pH 7.4 (with KOH).

Skin preparation

Heat-stripped stratum corneum was used in all experiments (area exposed to the electrical field=0.7 cm$^2$) (Prausnitz et al., PNAS, v. 90, p. 10504–10508, 1993). The skin was obtained from the abdomen, arm, or back of adult human cadavers. Prior to heat-stripping the skin was stored at –70° C. for one to six months. After heat-stripping, the skin was stored at 4° C. in a 95% humidity environment.

Pulse application

As in previous studies (see Prausnitz et al., ibid) high-voltage pulses were delivered using an exponential pulser (Electroporation System 600, BTX Industries, San Diego, Calif.) modified for automated control. The electrode design, orientation and permeation chambers have been described previously. The pulse time constant $\tau_{pulse}$ was 1.0 ms with 0.1 ms variation during an experiment.

Image acquisition and gel trapping of transported beads

In order to demonstrate that beads appearing on the other (epidermal) side of the skin were actually moved across the skin, the gel-trapping method described by Pliquett, U. F., Zewert, T. E., Chen, T., Langer, R., and Weaver, J. C., "Imaging of Fluorescent Molecules and Small Ion Transport Through Human Stratum Corneum During High-Voltage Pulsing: Localized Transport Regions are Involved" *J. Biophys. Chem.* 58:185–204, 1996, was used to trap (and thereby localize) the beads transported across the skin. This involved the placement of a 300 μm thick layer of 2% Type VII agarose adjacent to the skin on the stratum corneum side. The beads were supplied at a high concentration on the epidermal side, so that beads move through both a thin epidermal layer and the stratum corneum. The beads trapped within the gel layer were observed by microscopy.

A biocular fluorescence microscope (Olympus BH-2) was used, together with an Olympus OM2 camera.

RESULTS

The goal of this example was to transport beads across skin that was modified by the introduction of a reducing agent. Experiments using skin with and without reducing agent (sodium thiosulfate) showed that many beads were transported across the skin at localized sites only if the reducing agent had been used. Examination by microscopy showed that more than 50–100 beads were transported at a typical participating site for a pulse protocol of 100 pulses of 600-V amplitude and 1-ms time constant, at one pulse per 5 seconds. These results demonstrate introduction of a modifying agent such that large numbers of charged beads were transported across the stratum corneum of the skin.

EXAMPLE 5

The invention was also illustrated by experiments that used electrically charged beads and electrical pulses to demonstrate entry of such beads into the stratum corneum.

Methods

Full thickness human skin was stored up to 10 days at 4° C. on filter paper moistened with phosphate-buffered saline (PBS; pH 7.4; 150 mM total salts; Sigma Chemical Co., St. Louis, Mo.). Skin was loaded into side-by-side chambers (Crown Glass Co., Somerville, N.J.) (see Friend, J. Controlled Release, v. 18, p. 235–248, 1992) containing well-stirred PBS at 37° C. To ensure intact skin barrier function, only skin samples which had resistance>50 kΩ cm$^2$ were used.

After 1 h, PBS was emptied from the chambers and replaced with 1 mM calcein (Sigma) in PBS in the donor compartment (facing the stratum corneum, 0.7 cm$^2$ exposed skin) and fresh PBS in the receptor compartment (facing the dermis). Highly charged, carboxylate-modified latex microspheres (0.01, 0.1, 0.2, 0.5, and 2.0 μm diameters; FluoSpheres, red fluorescent, Molecular Probes, Inc., Eugene, Oreg.) were used as transport probes. The microspheres were added to the donor compartment with the calcein at 0.1 mg beads/ml. After>1 of passive exposure to calcein, fresh PBS was placed in the receptor compartment and electrical protocols were applied for 1 h. Within 10 min after termination of electrical exposure, skin samples were gently removed from the permeation chambers, rinsed with PBS, rapidly frozen in liquid nitrogen, and stored at −80° C. until analysis.

Our electrical apparatus has been discussed previously (Prausnitz et al., PNAS 90:10504–10508, 1993). Ag/AgCl electrodes (In Vivo Metrics, Healdsburg, Calif.), each located ~3 cm from the skin, were used to apply either (a) exponential-decay electric pulses (exponential-decay time constant, $\tau_{pulse}$=1.1 ms; ECM 600, BTX, San Diego, Calif.) at a rate of 12 pulses per minute or (b) a continuous, constant current (Model APH 1000M, Kepko, Flushing, N.Y.). The negative electrode was in the donor compartment, while the positive electrode was in the receptor compartment. Reported pulse voltages are averaged transdermal values determined during the first pulse of each hour-long sequence of pulses. Because significant voltage drops occurred within donor and receptor solution and electrodes, the voltage applied across the electrodes was approximately three-fold higher than the transdermal value (Prausnitz et al., PNAS, v. 90, p. 10504–10508, 1993; Bose, M. S. Thesis, MIT, 1994).

The skin samples were later warmed to room temperature, subjected to post-treatment staining, and then examined by scanning confocal fluorescence microscopy. We used a MRC-600 confocal system (Bio-Rad Microscience, Hercules, Calif.) mounted on a Nikon upright microscope (Optiphot-2, Nikon, Melville, N.Y.) and equipped with a krypton/argon mixed-gas laser that provided excitation wavelengths of 488, 568 and 647 nm. The objective lenses used were the Nikon CF Fluor 10× dry (NA of 0.5), which provided an overview of the specimen, and the Nikon CF Fluor 40× oil (NA of 1.30), employed for detailed examination. We used Nikon immersion oil, with an index of refraction of 1.515, and #1 circular coverslips (Fisher Scientific, Pittsburgh, Pa.) for all experiments. Photographs were obtained from a dedicated photorecord system (Image Corder Plus, Focus Graphics, Foster City, Calif.).

Two fluorescent probe molecules were utilized for post-treatment tissue staining. Nile Red (Molecular Probes) is almost nonfluorescent in water and other polar solvents, but exhibits strong red fluorescence when in a nonpolar environment. DiI, (Molecular Probes), another lipophilic dye, is excited by the 568 nm confocal laser line and emits orange fluorescence. Post-treatment staining with Nile red was performed by diluting a stock solution of 0.5 mg/ml Nile Red in acetone into 75% glycerol in water to a final concentration of 12.5 μg/ml. Post-treatment staining with DiI was performed by diluting a stock solution of 10 mM DiI in DMSO into deionized water to a final concentration of 10 μM. A drop of either solution sufficient to cover the skin sample was placed on the skin for >15 min and then washed off with PBS.

The skin sample to be viewed was mounted in a specially-designed piston-cylinder sample chamber. K1/K2 dual filter blocks (Bio-Rad) were used. This permitted simultaneous excitation of the sample at 488 and 568 nm, and concurrent collection of the green and red fluorescence in separate channels. Optical sectioning of the skin is restricted to its outer 20 μm due to light scattering and absorption of the emitted fluorescence (Cullander, Adv. Drug Deliv. Rev., v. 9, p. 119–135, 1992) and refractive index mismatch of the skin and microscope optics (Heller, 1993).

Results and Discussion

Pulsing at 300 V across the skin led to the appearance of bright regions containing dark interiors, viz. fluorescent "rings." These rings were never observed in constant current or lower voltage (40–75 V) pulsed samples and were always found in samples pulsed at 300 V.

To further characterize the dark ring interiors, electrically treated skin samples were passively stained with nonspecific lipophilic dyes, either Nile Red or DiI, before imaging with the confocal microscope. Because these dyes fluoresce in the red, they could be distinguished from calcein's green fluorescence. In low magnification images containing rings of calcein fluorescence, the fluorescence from the lipophilic stain displayed neither bright areas nor rings. Examination of rings under higher magnification showed that the ring interiors displayed no calcein fluorescence but did display red fluorescence, suggesting that the ring interiors contained lipophilic material. The nature of the ring interiors was further investigated by including red-fluorescent, highly negatively charged latex microspheres with the calcein in the donor compartment during high-voltage pulsing. While some of the microspheres were found distributed over the surface of the stratum corneum, most were found packed within the ring interiors. The rings appear to be located mainly in the stratum corneum itself, and are not associated with appendages.

Pulsing at higher transdermal voltage (300 V) has been shown to cause large, and only partially reversible increases in flux (Prausnitz et al., 1993). In this study with the confocal microscope, localized regions of transport were also evident, but had ring-like shapes. The bright outer portion of the rings probably correspond to sites of calcein flux. Moreover, fluorescence seen within keratinocyte interiors in these regions suggests the presence of a transcellular route of transport.

The presence of faint fluorescent outlines within the dark areas suggests that transport did occur in this region, but that very little calcein was present at the time of imaging. Subsequent experiments in a related study (Pliquett, U., Zewert, T. E., Chen, T., Langer, R., and Weaver, J. C., "Imaging a Fluorescent Molecule and Small Ion Transport Through Human Stratum Corneum During High-Voltage Pulsing: Localized Transport Regions are Involved" J. Biophys. Chem. 58:185–204, 1996) have shown that sites of fluorescence in stratum corneum correspond to sites of transdermal transport. Further, the lipophilic dyes show the presence of what is probably cellularly associated lipid within these dark areas. The most significant finding is the clustering of charged microsphere within the dark regions. Our interpretation is that these dark areas, which appear to contain cellular material, represent sites where transport of calcein and microspheres occurred during pulsing. Subsequently, microspheres remained in the dark regions at the time of imaging, but calcein did not. The selective removal of calcein could be caused by local tissue structural changes of dimensions greater than calcein (1.2 nm diameter), but less than the microspheres (10 nm diameter of the smallest microspheres).

These results show that some beads (microspheres) enter deeply into the skin's stratum corneum, due solely to electrical pulsing that causes electroporation.

EXAMPLE 6

Materials and Methods

The invention was illustrated for the case that charged beads alone were introduced into the skin by electrical pulsing that is believed to cause electroporation of skin.

Solution Preparation

Phosphate-buffered saline (PBS), composed of 138 mM NaCl (Sigma Chemical Co., St. Louis, Mo.), 8.1 mM $Na_2HPO$ (Mallinckrodt, Paris, Ky.), 2.7 mM KCl (Mallinckrodt), and 1.1 mM $KH_2PO_4$ (Mallinckrodt) in distilled water was adjusted to pH 7.4 with HCl (Mallinckrodt) and NaOH (Mallinckrodt), then placed under vacuum for >30 min. to remove dissolved gasses.

The stock slide mounting solution consisted of 0.5 mg/ml of Nile Red (Molecular Probes, Inc., Eugene, Oreg.) dissolved in acetone (Mallinckrodt). Before the experiment, the stock solution was diluted in a solution of 75\% glycerol (Mallinckrodt) in water to a concentration of 12.5 $\mu$g/ml to make the mounting solution.

Human Skin Preparation

Before use, the epidermis was removed from the dermis and subcutaneous fat by heat-stripping. The epidermis is a well-established model for transdermal drug delivery, since it is the main barrier for molecular transport (Bronaugh and Maibach (Eds.) *Percutaneous Absorption, Mechanisms—Methodology—Drug Delivery*, Marcel Dekker, New York, 1989; Hadgraft and Guy (Eds.), *Transdermal Drug Delivery: Developmental Issues and Research Initiatives*, Marcel Dekker, New York, 1989).

Cadaver skin was stored at −80° C. for up to 6 months before use. The skin was harvested from the abdomen, thighs, and back. The skin was thawed to room temperature, then heated in water at 60° for 2 min. The epidermis was gently scraped off the dermis and stored at 4°, 95% humidity for up to 10 days (Gummer, C. L., "The In Vitro Evaluation of Transdermal Delivery," in Transdermal Drug Delivery: Developmental Issues and Research Initiatives J. Hadgraft and R. H. Guy, Eds., Marcel Dekker, New York, 177–186, 1989).

Bead characteristics

Green fluorescent (470 nm excitation, 505 nm emission), negatively charged, carboxylate-modified polystyrene latex beads (Sigma) diluted 10:1 in PBS to a final solution concentration of 0.25% solids, giving each donor solution the same total volume of beads. Surface charges given in units of the electron's charge (Sigma) and final bead concentrations are given in the following table:

| Bead diameter $\mu$m | Charge | Final Concentration (beads/ml) |
|---|---|---|
| 2.16 | $-2.77 \times 10^7$ | $4.7 \times 10^8$ |
| 1.01 | $-4.58 \times 10^7$ | $4.6 \times 10^9$ |
| 0.431 | $-2.33 \times 10^6$ | $6.0 \times 10^{10}$ |
| 0.105 | $-1.39 \times 10^5$ | $4.1 \times 10^{12}$ |
| 0.035 | $-4.05 \times 10^3$ | $1.1 \times 10^{14}$ |

Experimental Apparatus

The skin was placed in side-by-side diffusion chambers (Crown Bio Scientific) (Friend, J. Controlled Release, v. 18, p. 235–248, 1992), with the stratum corneum (top surface of the skin) facing the donor compartment. The chambers were fitted with silver electrodes flow-protected by polyacrylamide gel. The application of high-voltage pulses causes the electrodes to release electrochemical by-products, and the flow protection prevents contamination of the donor and receptor solutions. Polyacrylamide gel was chosen since it is electrically conducting (1$\Omega$), inert, easy to prepare, and does not readily allow by-products or beads to diffuse across.

The flow-protected electrodes were made by soldering silver wire, ~0.5 cm long, to copper bell wire. The solder and exposed wire was covered by nonconducting silicone (General Electric, Waterford, N.Y.), so only silver wire was exposed. A piece of Tygon tubing, $\frac{1}{32}$" ID, and the silver electrode were inserted into a truncated 100 $\mu$l pipette tip. The top of the pipette was then sealed off with epoxy (Devcon, Wood Dale, Ill.).

Polyacrylamide gel was prepared in the chambers as follows. Plastic tubing was inserted into each chamber half and sealed in place with parafilm (American National Can, Greenwich, Conn.). Polyacrylamide solution, consisting of 0.75 g of 19:1 acrylamide:bis(N,N'-methylene-bis-acrylamide) powder (Bio-Rad, Hercules, Calif.), 43.75 $\mu$l of 440 mM $(NH_4)_2S_2O_8$ solution (Mallinckrodt), and 3 $\mu$l of N,N,N',N'-tetramethylethylenediamine (Bio-Rad) in 5 ml PBS, was poured into the chamber and allowed to harden. After the gel hardened, the tubing and parafilm were removed, leaving behind a clear channel through the gel.

During the experiment, PBS was pumped at the rate of ~0.5 ml/min through the chamber, thereby removing any electrode by-products generated by either high-voltage pulsing or continuous dc current.

The donor compartment was filled with bead solution and the receptor compartment was filled WITH PBS. Both compartments were continuously stirred by magnetic stir bars.

High-voltage exponential pulses were delivered by an exponential pulser (Electroporation System 600, BTX Industries, San Diego, Calif.). Because the beads were negatively charged, the negative electrode was placed in the donor compartment on the stratum corneum side, and the positive electrode was placed in the receptor compartment, just as in other experiments involving transport of negatively charged beads or molecules. Current delivered to the skin during the pulse was measured by measuring the voltage drop across a 1.2Ω power resistor placed in series with the side-by-side chambers. The voltage drop of the resistor was measured by a 10× probe connected to a digital oscilloscope (Hewlett Packard 54601, Hewlett Packard, Palo Alto, Calif.), allowing the current to be calculated by Ohm's law. A custom-built device measured the voltage drop at 1000× across the inner electrodes in the side-by-side chamber. This device was also connected to the oscilloscope. By knowing the resistance of PBS (by pulsing the chambers without any skin), the current delivered during the pulse, and the voltage drop across the inner electrodes during the pulse, the voltage drop across the skin could be calculated (Pliquett, U., Langer, R., and Weaver, J. C., "The Change in The Passive Electrical Properties of Skin due to Electroporation" *Biochem. Biophys.* Acta 1239:111–121, 1995).

A constant current for transport was delivered to the side-by-side chambers by a custom-built device.

Immediately after pulsing, the chambers were emptied and the skin carefully removed for microscopy. The skin was gently placed on a microscope slide (Gold Seal Rite-On, No. 3050, Clay Adams, Becton Dickinson Labware, Franklin Lakes, N.J.) and a drop of mounting solution added. A 22×22 No. 1 cover slip (Clay Adams) was carefully placed on top and sealed in place with nail polish (Hard as Nails, Sally Hansen, Del Laboratories, Farmingdale, N.Y.).

A biocular fluorescence microscope (Olympus BH-2, Olympus, Woodbury, N.Y.) was used to examine the skin. This microscope allowed simultaneous fluorescence and light illumination of the slides at 4× and 10× magnification. The fluorescent beads could be readily seen on the surface of the skin. Photomicrographs were taken using a camera (Olympus OM2, Olympus) mounted on the microscope.

Skin Experimental Protocol

Prepared, stored skin epidermis was loaded into the side-by-side chambers, with the stratum corneum facing the donor compartment. The resistance of the skin was checked by applying a 1 μA ac current across the skin and measuring the resulting voltage drop, using a custom built device. The resistance was then calculated by Ohm's law. Skin with resistance <100 kΩ/cm$^2$ was not used (Prausnitz, Ph. D. Thesis, MIT, 1994).

The donor and receptor compartments were filled with their respective solutions and the apparatus was allowed to sit for one hour to fully hydrate the skin (Prausnitz et al., PNAS, v. 90, p. 10504–10508, 1993) and check for leaks. Bead diameters in the donor compartment were varied between 0.035 and 2.16 μm; the bead concentration was kept constant at 0.25\% solids.

After one hour, passive controls (no pulsing) and electrical treatments were applied. Electrical treatments included 1 and 10 mA/cm$^2$ constant current application, and high-voltage exponential pulsing, with time constants between 1 and 15 ms and transdermal voltages between about −100 and 100 V. (All voltages will be given as transdermal values.)

After one hour of electrical treatment, the skin was carefully removed from the side-by-side chambers and prepared for microscopy studies.

Results and Discussion

No bead clustering observed under passive conditions

After passive treatment of the skin (no pulsing or constant current) with 2.16 μm diameter beads for 2 h, a sparse, mostly homogenous dispersion of beads was seen on the top surface of the skin under microscopy. Similar results were obtained with 1.01, 0.431, and 0.035 μm diameter beads. Without an external driving force, the beads interact only very weakly with the stratum corneum and do not cluster.

Constant current causes clustering of beads at hair follicles

Application of constant current (1 mA/cm$^2$) with 2.16 μm diameter beads of the skin for 1 h gave a sparse, mostly homogenous dispersion of beads on the top surface of the skin. Moderate clustering of the beads was found at the tips of the hair follicles. Similar results were found with 1.01 and 0.105 μm diameter beads. However, under constant current of 10 mA/cm$^2$ using 2.16 μm beads for 1 h, very large concentrations of beads were found at the tips of the hair follicles. The rest of the surface of the skin showed a dense, homogeneous dispersions of beads.

Ion transport across the skin during constant current application is believed to occur primarily across sweat ducts and hair follicles (Scott et al., Pharm Res., v. 10, p. 1699–1709, 1993). Our results are consistent with this interpretation. The charged beads presumably follow the electric field lines and cluster near hair follicles, where most of the current crosses the skin. This effect is more pronounced at higher applied constant currents.

Bead cluster sizes increase with longer time constant

High-voltage exponential pulses were applied to the skin at ~80 V, once every 5 s for 1 h, using 2.16 μm diameter beads in the donor compartment. Time constants used in this series of experiments varied from 1 ms to 15 ms. Clusters of beads were found on the surface of the stratum corneum, with the size of the clusters increasing with the time constant, up to 300 μm in diameter for $\tau_{pulse}$=15 ms. The number of clusters observed per unit area decreased with increasing time constants. The clusters were found dispersed randomly over the surface. No correlation was found with either sweat ducts or hair follicles.

With the application of high-voltage pulses using a time constant of 15 ms, red regions were found in the skin in the centers of the bead cluster areas. These regions appeared red due to the presence of the Nile Red stain, indicating that these areas were filled with lipophilic material.

The appearance of clusters of beads on the surface of the skin is similar to the results obtained by Pliquett, U., Zewert, T. E., Chen, T., Langer, R., and Weaver, J. C., "Imaging of Fluorescent Molecules and Small Ion Transport Through Human Stratum Corneum During High-Voltage Pulsing: Localized Transport Regions are Involved," *J. Biophys. Chem.*, 58:185–204, 1996 who described the appearance of "localized transport regions" (LTR's) on the surface of the skin after high-voltage pulsing, created by using calcein (−4 charge) or sulforhodamine (−1 charge) in the donor compartment. The LTRs were described as reaching diameters of approximately 40 to 80 μm. However, larger LTR's have recently been found to occur as the pulse time constant is increased. Because the beads were also negatively charged, the same electrical force is likely to be transporting the molecules and the beads to the surface of the skin. During high-voltage pulsing, localized ion currents are believed to cross the skin within LTR's for calcein and sulforhodamine (Pliquett, U., Zewert, T. E., Chen, T., Langer, R., and Weaver, J. C., "Imaging of Fluorescent Molecules and Small Ion Transport Through Human Stratum Corneum During High-Voltage Pulsing: Localized Transport Regions are Involved," *J. Biophys. Chem.*, 58:185–204, 1996). Thus, localized ion currents across the surface of the skin, created during high-voltage pulsing, could also be responsible for transporting beads to the surface of the skin and depositing many of them in clusters, with some beads being transported across the skin.

The red regions found on the surface of the skin, after high-voltage pulsing with a time constant of 15 ms, appear similar to the results of Prausnitz et al., who described the appearance of "fluorescent rings." These fluorescent rings were observed on the surface of the skin after high-voltage pulsing at ~300 V with calcein in the donor solution. The interiors of the fluorescent rings displayed red fluorescence after staining of the skin with Nile Red. The fluorescent rings were located primarily in the stratum corneum and did not appear to be associated with hair follicles or sweat ducts.

Bead clusters found above 70 V

High-voltage exponential pulses were applied to the skin every 5 s for 1 h, with a time constant of 5 ms, using 2.16 µm beads in the donor compartment. Transdermal voltages in this series of experiments were varied from about –100 to 120 V. A time constant of 5 ms was chosen because 1 ms gave very small bead clusters. Clusters of beads were found on the surface of the stratum corneum, with more bead clusters observed at larger voltages. The size of the bead clusters did not significantly change for different voltages. Very few bead clusters were observed on the skin after pulsing at ~70 V. No bead clusters were observed at voltages less than ~70 V, including reverse pulsing at about –100 V (pulsing with the positive electrode in the donor compartment and the negative electrode in the receptor compartment, instead of vice versa).

These results are consistent with the idea that high-voltage pulsing of the skin below ~75 V does not cause increased molecular or ionic transport (Pliquett, U., Langer, R. and Weaver, J. C., "The Change in the Passive Electrical Properties of Skin due to Electroporation," *Biochem. Biophys. Acta* 1239:111–121, 1995). As transdermal voltage was increased, greater numbers of bead clusters could be found on the stratum corneum, which is again similar to LTR behavior for calcein and sulforhodamine observed by Pliquett, U. F., Zewert, T. E., Chen, T., Langer, R., and Weaver, J. C., "Imaging of Fluorescent Molecules and Small Ion Transport Through Human Stratum Corneum During High-Voltage Pulsing: Localized Transport Regions are Involved," *J. Biophys. Chem.* 58:185–204, 1996 who found that the number of LTR's observed increased as voltage was increased, while the size of LTR's remained approximately constant.

Because the creation of both bead clusters and LTR's appears similar under various conditions, similar localized electroporation is probably responsible for their creation.

Similar bead clustering observed for different sizes of beads

High-voltage exponential pulses were applied to the skin, with a voltage of ~100 V and a time constant of 5 ms. The pulses were applied every 5 s for 1 h. The sizes of the beads in the donor compartment were varied in this set of experiments from 0.035 to 2.16 µm in diameter, at a concentration of 0.25% solids. Bead clusters were found on the surface of the stratum corneum after 1 h of pulsing. In each case, the bead clusters appeared similar, with the clusters being 150 µm in diameter.

As mentioned above, results similar to the 2.16 µm bead results were obtained during passive controls and constant current application, using 1.01, 0.431, 0.105, and 0.035 µm beads.

The size or charge of the beads does not appear to have a major effect on the formation of bead clusters on the surface of the skin during high-voltage pulsing. It appears that the formation of bead clusters or LTR's depends more on the applied pulses, rather than the physical properties of the molecules or beads.

Thus, high-voltage pulsing appears to create regions where ion currents cross the surface of the skin. These regions are associated with the clustering of many beads at the surface, with some probably penetrating into and/or across the skin, and are also associated with transdermal transport of charged molecules due to localized structural changes in the skin.

EXAMPLE 7

Heat stripped human skin from the same donor was placed in each of the two permeation chambers connected electrically in series, so that the application of pulses produced the same current pulse through both pieces of skin. One chamber contained guanidine (Sigma G-4505, Lot 45H5739) provided at a concentration of 6M in phosphate buffered saline at pH 7.8 while the other chamber was used with only phosphate buffered saline to provide a control. Exponential pulses ($\tau_{pulse}$=1 ms) were applied at 5 second interpulse intervals, using a peak voltage across both chambers of 2,000 V (approximately 1,000 V across the electrodes of each chamber).

The green fluorescence (GF) of calcein and red fluorescence (RF) of sulforhodamine were corrected for the affect of guanidine on their fluorescence (measured in photon cps=counts per second in arbitrary units). This was accomplished by using dilute solutions of calcein and sulforhodamine, and comparing the fluorescence emission of these solutions to solutions that also contained 6M guanidine. For calcein, the fluorescence signal of the solution without guanidine was $4.4 \times 10^6$ cps but the solution with 6M guanidine had GF of $3.0 \times 10^6$ cps. In the case of sulforhodamine, the solution without guanidine had RF of $2 \times 10^6$ cps, and the solution with guanidine had about half this value, viz $1.1 \times 10^6$ cps. The measurements in the pulsed skin experiments were therefore corrected by multiplying the GF of calcine by a factor of 4.4/3.0=1.47 and the RF of sulforhodamine by a factor of 2/1.1=1.82.

RESULTS OF EXPERIMENT ONE

Immediately after pulsing for one hour

|  | Calcein | Sulforhodamine |
| --- | --- | --- |
| Control | $1.8 \times 10^7$ cps | $6.08 \times 10^6$ cps |
| 6M guanidine | $3.8 \times 10^5$ cps | $3.2 \times 10^5$ cps |

One hour after pulsing has stopped (passive transport by diffusion)

|  | Calcein | Sulforhodamine |
| --- | --- | --- |
| Control | $7.4 \times 10^5$ cps | $3.5 \times 10^6$ cps |
| 6M guanidine | $8.4 \times 10^4$ cps | $1.5 \times 10^5$ cps |

Three hours after pulsing has stopped (passive transport by diffusion)

|  | Calcein | Sulforhodamine |
| --- | --- | --- |
| Control | $3.6 \times 10^5$ cps | $1.7 \times 10^6$ cps |
| 6M guanidine | $1.6 \times 10^5$ cps | $3.8 \times 10^5$ cps |

RESULTS OF EXPERIMENT TWO

Immediately after pulsing for one hour

|  | Calcein | Sulforhodamine |
| --- | --- | --- |
| Control | $5.9 \times 10^6$ cps | $5.2 \times 10^6$ cps |
| 6M guanidine | $2.04 \times 10^6$ cps | $1.1 \times 10^6$ cps |

One hour after pulsing has stopped (passive transport by diffusion)

|  | Calcein | Sulforhodamine |
| --- | --- | --- |
| Control | $3.7 \times 10^5$ cps | $2.3 \times 10^6$ cps |
| 6M guanidine | $1.9 \times 10^5$ cps | $4.1 \times 10^5$ cps |

Three hours after pulsing has stopped (passive transport by diffusion)

|  | Calcein | Sulforhodamine |
| --- | --- | --- |
| Control | $1.9 \times 10^5$ cps | $1.4 \times 10^6$ cps |
| 6M guanidine | $1.2 \times 10^5$ cps | $3.9 \times 10^5$ cps |

These experiments provide an example of the use of a modifying agent that alters molecular transport across skin such that the transport is reduced. Our hypothesis is that electroporation provides access of guanidine into the interior of corneocytes by creating new aqueous pathways, and that guanidine, a denaturing agent, expands intermediate filaments of the keratin matrix within the corneocyte's interiors, such that this expansion increases steric hindrance to molecular transport.

Equivalents

Those skilled in the art will recognize, or be able to ascertain using no more than routine experimentation, many equivalents to specific embodiments of the invention described specifically herein. Such equivalents are intended to be encompassed in the scope of the following claims.

We claim:

1. A method of modifying epidermis for transport of a material by electroporation, comprising the steps of:
   a). applying to epidermis a modifying agent which can enter or pass across the epidermis while the epidermis is in an electroporated state and that, upon entry into the epidermis, will modify the epidermis to thereby cause an altered rate of transport of a material across said epidermis; and
   b). electroporating the epidermis, thereby at least a portion of the agent enters the electroporated epidermis, thereby modifying the epidermis to cause an altered rate of transport of a material across said epidermis.

2. The method of claim 1, wherein the agent decreases the rate of transport of the material into the epidermis.

3. The method of claim 1, wherein the agent increases the rate of transport of the material into the epidermis.

4. The method of claim 1, wherein the agent modifies epidermis by physiochemically disrupting a keratin component of the epidermis.

5. The method of claim 1, wherein the agent is a reducing agent.

6. The method of claim 5, wherein the reducing agent is sodium thiosulfate.

7. The method of claim 5, wherein the reducing agent is glutathione.

8. The method of claim 1, wherein the agent is denaturing agent.

9. The method of claim 1, wherein the agent is an enzyme that catalyzes a reaction that disrupts a barrier of said epidermis.

10. The method of claim 1, further including the step of applying the material to said epidermis at a point proximate to said agent.

11. The method of claim 10, wherein said material is applied to the epidermis after the agent has entered the epidermis.

12. The method of claim 10, wherein said material is a protein.

13. The method of claim 10, wherein said material is a nucleic acid.

14. The method of claim 10, wherein said material is a particle.

15. The method of claim 14, further including the step of measuring transmission of light through epidermis containing the particle.

16. The method of claim 15, wherein the particle comprises an optical indicator.

17. The method of claim 16, wherein a ratiometric indicator is employed to measure transmission of light through the epidermis containing the particle.

18. The method of claim 17, wherein at least two particles of different size are employed, and wherein at least one particle comprises an optical standard bead and at least one particles comprises an optical indicator bead, whereby a non-spectral measurement can be made of the particles contained in the epidermis.

19. The method of claim 18, wherein said optical indicator beads are responsive to an environmental condition selected from the group consisting of oxygen partial pressure, carbon dioxide partial pressure, pH and temperature.

20. A method of claim 15, wherein the particle includes at least one reagent that reacts with a component contacting the particle and to thereby indicate a concentration of said environmental component.

21. The method of claim 14, wherein the agent and material are components of a composition applied to said epidermis.

22. The method of claim 14, further including the step of extracting said particle from the epidermis.

23. A method of claim 14, wherein said particle causes formation of a pathway in said epidermis during entry into the epidermis.

24. A method of claim 23, wherein said particle is directed through the epidermis to a tumor beneath said epidermis, whereby the pathway formed by entry of the particle causes pressure within the tumor to be reduced.

25. A method of claim 24, further including the step of applying pressure to the tumor by application of ultrasound to the tumor.

26. A method of claim 14, further including the step of applying an electric field across the epidermis, whereby iontophoretic transport of the material across the epidermis is increased.

27. The method of claim 14, wherein the particle is a bead.

28. The method of claim 27, further including the step of electroporating the epidermis after the agent has entered the epidermis, whereby said material applied to the epidermis enters the epidermis.

29. The method of claim 27, wherein the bead includes at least one drug.

30. The method of claim 27, wherein the particle is a microorganism.

31. A method of claim 14, wherein the particle is directed into a stratum corneum layer of said epidermis.

32. The method of claim 11, further including the step of applying a force to the modified epidermis, whereby the material enters the modified epidermis containing the agent.

33. The method of claim 32, wherein said force includes a mechanical force.

34. The method of claim 33, wherein said force includes electrocompression.

35. A method of claim 32, wherein the force is a magnetic force.

36. The method of claim 1, further including the step of measuring the electrical resistance of the epidermis after said epidermis is electroporated.

37. The method of claim 1, wherein the agent carries an electrical charge.

38. The method of claim 37, wherein the agent is a cation.

39. The method of claim 37, wherein the agent is an anion.

40. A method for transporting a material into an epidermis, comprising the steps of:
   a). applying to epidermis a composition of at least one electrically charged modifying agent which can enter of pass across the epidermis while said epidermis is in an electroporated state and that, upon entry into the epidermis, will modify the epidermis to thereby cause an altered rate of transport of a material of the composition, and at least one material to be transported across the epidermis by electroporation; and
   b). electroporating the epidermis at said composition, whereby at least a portion of the electrically charged agent enters the epidermis to cause an altered rate of transport of the material across the epidermis.

41. A method of claim 40, wherein said electrically charged agent carries an amount of charge that changes as said agent is directed into the epidermis.

42. A method of claim 41, wherein the charge associated with the electrically charged agent changes as a consequence of a difference of the pH within said epidermis from that of a composition from which said agent is transported.

43. A method of claim 41, wherein the charge of the electrically charged agent changes upon entry into the epidermis as a consequence of interaction with an enzyme within said epidermis.

44. A method of modifying a tissue for transport of a material by electroporation, comprising the steps of:
   a). electroporating a region of tissue; and
   b). applying to said region a modifying agent which can enter or pass across said region of tissue while said region is in an electroporated state and that enters the electroporated tissue and modifies said tissue, whereby a material applied to said region will be transported across the modified tissue at a different rate than into electroporated tissue that is not modified by said agent.

45. The method of claim 44, further including the step of applying said material to said region of tissue.

46. The method of claim 45, further including the step of applying an electric field across the tissue, whereby iontophoretic transport of the material across the tissue is increased.

47. The method of claim 46, further including the step of applying at least one electrical pulse to said region, whereby said region is further electroporated, thereby causing additional transport of material at said region.

48. The method of claim 44, further including the step of withdrawing the material from the tissue.

49. The method of claim 48, wherein said tissue is epidermis.

* * * * *

UNITED STATES PATENT AND TRADEMARK OFFICE
CERTIFICATE OF CORRECTION

PATENT NO. : 5,911,223
DATED : June 15, 1999
INVENTOR(S) : James C. Weaver, Thomas E. Zewert, Uwe Pliquett, Rita Vanbever, Mark R. Prausnitz, Tani Chen, Christopher Cullander, Richard Guy and Robert S. Langer It is certified that error appears in the above-identified patent and that said Letters Patent is hereby corrected as shown below:

At Claim 1, Col. 27, line 57, delete "thereby" and substitute therefor --whereby--.

At Claim 40, Col. 29, line 28, delete "of" and substitute therefor --or--.

At Claim 40, Col. 29, line 37, after "epidermis" insert --, thereby modifying the epidermis--.

Signed and Sealed this

Fourteenth Day of March, 2000

*Attest:*

Q. TODD DICKINSON

*Attesting Officer*  Commissioner of Patents and Trademarks